US008124417B2

(12) United States Patent
Umezawa et al.

(10) Patent No.: US 8,124,417 B2
(45) Date of Patent: Feb. 28, 2012

(54) METHOD FOR ANALYZING NUCLEOBASES ON A SINGLE MOLECULAR BASIS

(75) Inventors: Yoshio Umezawa, Saitama (JP); Takahito Ohshiro, Saitama (JP)

(73) Assignee: Japan Science and Technology Agency, Saitama (JP)

( * ) Notice: Subject to any disclaimer, the term of this patent is extended or adjusted under 35 U.S.C. 154(b) by 199 days.

(21) Appl. No.: 11/794,294

(22) PCT Filed: Dec. 28, 2005

(86) PCT No.: PCT/JP2005/024285
§ 371 (c)(1),
(2), (4) Date: Aug. 20, 2007

(87) PCT Pub. No.: WO2006/070946
PCT Pub. Date: Jul. 6, 2006

(65) Prior Publication Data
US 2009/0155917 A1    Jun. 18, 2009

(30) Foreign Application Priority Data
Dec. 28, 2004   (JP) ................................ 2004-381406

(51) Int. Cl.
*G01N 33/00*    (2006.01)
*C07D 473/00*   (2006.01)
(52) U.S. Cl. ........... 436/94; 544/276; 544/299; 544/311

(58) Field of Classification Search .................. 436/94; 544/276, 299, 311
See application file for complete search history.

(56) References Cited

FOREIGN PATENT DOCUMENTS
GB           2235049    *  2/1991

OTHER PUBLICATIONS

T. Nishino et al., "Selective Observation of Hydroxy and Carboxylate Moieties by Scanning Tunneling Microscopy using Chemically Modified Tips with Differing Extents of Hydrogen Bond Acidity or Basicity", Journal of Electroanalytical Chemistry, 550-551, pp. 125-129, 2003.
T. Ohshiro et al., "Complementary Base-Pair-Facilitated Electron Tunneling for Electrically Pinpointing Complementary Nucleobases", PNAS, vol. 103, No. 1, pp. 10-14, Jan. 3, 2006, Epub Dec. 22, 2005.

* cited by examiner

*Primary Examiner* — Krishnan S Menon
*Assistant Examiner* — Rebecca M Fritchman
(74) *Attorney, Agent, or Firm* — Wenderoth, Lind & Ponack, L.L.P.

(57) ABSTRACT

A method is herein presented for analyzing nucleobases on a single molecular basis (a single molecule detection), which comprises scanning a molecular tip chemically modified with the complementary nucleobase on the nucleobases, and measuring the tunneling currents between the scanned nucleobases and the molecular tips with scanning tunneling microscopy.

5 Claims, 7 Drawing Sheets

US 8,124,417 B2

METHOD FOR ANALYZING NUCLEOBASES ON A SINGLE MOLECULAR BASIS

This application is a U.S. national stage of International Application No. PCT/JP2005/024285 filed Dec. 28, 2005.

TECHNICAL FIELD

The present invention relates to a method for analyzing nucleobases on a single molecular basis (a single molecule detection). More specifically, the present invention relates to a method for electrically pinpointing or typing a nucleobase in a nucleic acid, or electrically sequencing a nucleic acid by using scanning tunneling microscopy.

BACKGROUND ART

Recently, genomic structures of various species are being clarified due to technical development in molecular biology, and involvement of gene mutations have been revealed in many genetic diseases and viral diseases. Therefore, establishment of a method for detecting and analyzing a specific gene sequence or a mutant sequence is an important challenge in various fields such as medical science, medical jurisprudence, molecular biology and so on.

Among the gene mutations, attention is focused on single nucleotide polymorphisms (SNPs) since they are recognized as an important means for searching disease-related genes, diagnosis for disease risks, or analysis of drug responses and adverse drug reactions. Therefore, accurate and precise methods for detecting SNPs in a sample nucleic acid are needed.

As methods for detecting and analyzing gene mutations, capillary electrophoresis combined with fluorescence detection and DNA chips are popular. However, these methods have some problems such as a prolonged period of time for analysis.

Molecular tips in STM can directly detect intermolecular electron tunneling between sample and tip molecules, and reveal the tunneling facilitation through chemical interactions that provide overlap of respective electron wave functions, that is, hydrogen-bond, metal-coordination bond, and charge-transfer interactions, respectively (references 1-8). Nucleobase molecular tips were prepared by chemical modification of underlying metal tips with thiol derivatives of adenine, guanine, cytosine, and uracil, and the outmost single nucleobase adsorbate probes intermolecular electron tunneling to or from a sample nucleobase molecule. The inventors found that the electron tunneling between a sample nucleobase and its complementary nucleobase molecular tip was much facilitated compared to its non-complementary counterpart. The complementary nucleobase tip was thereby capable of electrically pinpointing each nucleobase. Chemically selective imaging using molecular tips may be coined "intermolecular tunneling microscopy" as its principle goes, and is of general significance for novel molecular imaging of chemical identities at the membrane and solid surfaces.

REFERENCES

1. Ito, T., Bühlmann, P. & Umezawa, Y. (1998) *Analytical Chemistry* 70, 255-259.
2. Ito, T., Bühlmann, P. & Umezawa, Y. (1999) *Analytical Chemistry* 71, 1699-1705.
3. Nishino, T., Bühlmann, P., Ito, T. & Umezawa, Y. (2001) *Physical Chemistry Chemical Physics* 3, 1867-1869.
4. Nishino, T., Ito, T. & Umezewa, Y. (2001) *Surface Science Letters* 490, L579-L584.
5. Ohshiro, T., Ito, T., Bühlmann, P. & Umezawa, Y. (2001) *Analytical Chemistry* 73, 878-883.
6. Nishino, T., Ito, T. & Umezewa, Y. (2002) *Analytical Chemistry* 74, 4275-4278.
7. Nishino, T., Ito, T. & Umezawa, Y. (2003) *Journal of Electroanalytical Chemistry* 550, 125-129.
8. Nishino, T., Ito, T. & Umezawa, Y. (2005) *Proceedings of the National Academy of Sciences of the United States of America* 102, 5659-5662.
9. Wiesendanger, R. & Güntherodt, H. J. (1993) *In Scanning Tunneling Microscopy III*, Springer Series in Surface Science 29; Springer-Verlag: Berlin
10. Ulman, A. (1996) *Chemical Reviews* 96, 1533-1554.
11. Seeler, J. L. & J. Jayawickramarajah (2005). *Chemical Communications*, 1939-1949.
12. Nielsen, P. E., Egholm, M., Berg, R. H. & Buchardt, O. (1991) *Science* 254, 1497-1500.
13. Wandlowski, T., Lampner, D. & Lindsay, S. M. (1996) *Journal of Electroanalytical Chemistry* 404, 215-226.
14. Li, W.-H., Haiss, W., Floate, S. & Nichols, R. J. (1999) *Langmuir* 15, 4875-4883.
15. Chen, Q., Frankel, D. J. & Richardson, N. V. (2002) *Langmuir* 18, 3219-3225.
16. Akiyama, R., Matsumoto, T. & Kawai, T. (1999) *The Journal of Physical Chemistry B* 103, 6103-6110.
17. Hamai, C., Tanaka, H. & Kawai, T. (2000) *The Journal of Physical Chemistry B* 104, 9894-9897.
18. Tanaka, H. & Kawai, T. (2003) *Surface Science Letters* 539, L531-L536.
19. Robins, R. K. (1958) *J. Am. Chem. Soc.*, 80, 6671-6679.
20. Koppel, H. C., Springer, R. H., Robins, R. K. & Cheng, C. C. (1961) *J. Org. Chem.*, 26, 792-803.
21. Wangenknecht, H.-A. (2003) *Angewandte Chemie International Edition* 42, 2454-2460.
22. Fink, H.-W. & Schönenberger, C. (1999) *Nature* 398, 407-410.
23. Lewis, F. D., Liu, X., Liu, J., Miller, S. E., Hayes, R. T. & Wasielewski, M. R. (2000) *Nature* 406, 51-53.
24. Grozema, F. C., Berlin, Y. A. & Siebbeles, L. D. A. (2000) *Journal of the American Chemical Society* 122, 10903-10909.
25. Berlin, Y. A., Burin, A. L. & Ratner, M. A. (2001) *Journal of the American Chemical Society* 123, 260-268.
26. Barnett, R. N., Cleveland, C. L., Joy, A., Landman, U. & Schuster, G. B. (2001) *Science* 294, 567-571.
27. Sessler, J. L., Sathiosatham, M., Brown, C. T., Rhodes, T. A. & Wiederrecht, G. (2001) *Journal of the American Chemical Society* 123, 3655-3660.

DISCLOSURE OF INVENTION

The present inventors found that the electron tunneling in STM between a nucleobase and its complementary nucleobase molecular tip was much facilitated compared to its non-complementary counterpart. The inventors found that this facilitated electron tunneling through the complementary base-pair with nucleobase molecular tips for selectively discriminating each of the complementary nucleobase from the other nucleobases (FIG. 1a).

The inventors have completed the present inventions from such novel findings.

The first invention is a method for analyzing nucleobases on a single molecular basis, which comprises scanning a molecular tip that is chemically modified with the complementary nucleobase on the nucleobases, and measuring the tunneling current between the scanned nucleobases and the molecular tip with scanning tunneling microscopy.

One embodiment of the first invention is a method for pinpointing a target nucleobase in a nucleic acid and comprises:

scanning a molecular tip on nucleobases in the nucleic acid, wherein the molecular tip is a metal tip chemically modified with a nucleobase complementary to the target nucleobase;

measuring the tunneling current between each nucleobase and the molecular tip with scanning tunneling microscopy; and pinpointing the target nucleobase as the nucleobase from which the tunneling current is facilitated upon scanning the molecular tip.

Another embodiment of the first invention is a method for typing of a target nucleobase and comprises:

scanning four molecular tips on the target nucleobase, wherein the four molecular tips are metal tips chemically modified with adenine, guanine, cytosine and thymine or uracil, respectively;

measuring the tunneling currents between the target nucleobase and each molecular tip with scanning tunneling microscopy; and determining the type of the target nucleobase that is complementary to the nucleobase on the molecular tip by which the largest tunneling current is measured.

Still another embodiment of the first invention is a method for sequencing a nucleic acid, which comprises:

scanning sequentially four molecular tips on nucleobases in the nucleic acid, in which the four molecular tips are metal tips chemically modified with adenine, guanine, cytosine and thymine or uracil, respectively;

measuring the tunneling currents between each nucleobase and each molecular tip with scanning tunneling microscopy; and determining the types of each nucleobase that are complementary to the nucleobase types on the molecular tip by which the largest tunneling currents are measured thereby sequencing the nucleic acid.

The second invention is a molecular tip for scanning tunneling microscopy, which is a metal tip chemically modified with adenine, guanine, cytosine, thymine or uracil.

The third invention is a set of four molecular tips for scanning tunneling microscopy, which consists of four metal tips chemically modified with adenine, guanine, cytosine and thymine or uracil, respectively.

Specific profiles, terms and concepts in each invention described here will be specified in the descriptions of the best mode and Examples of the inventions. Various technologies employed for carrying out the inventions can easily and reliably be conducted by those skilled in the art with referring to known references except for those whose references to be cited are indicated here. The technologies of the gene engineering and the molecular biology may be discussed for example by Sambrook and Maniatis in Molecular Cloning—A Laboratory Manual, Cold Spring Harbor Laboratory Press, New York, 1989; Ausbel F. M. et al., Current Protocols in Molecular Biology, John Wiley & Sons, New York, N.Y., 1995, or the references cited in these text books.

BEST MODE FOR CARRYING OUT THE INVENTION

Figure 1:
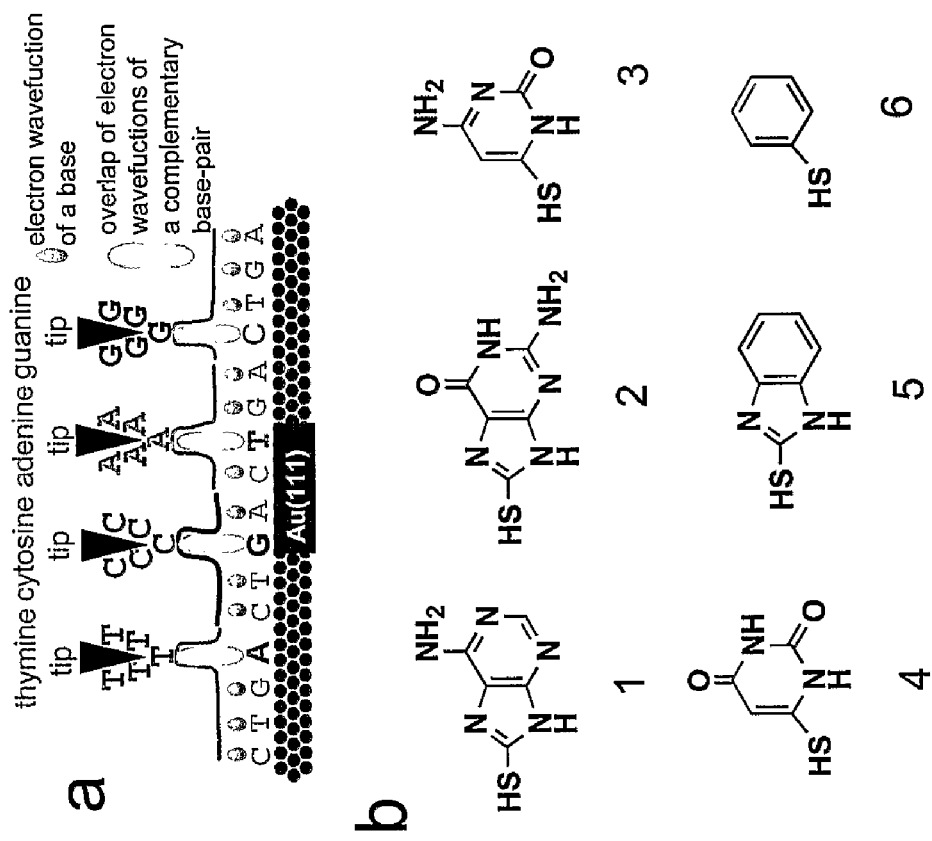
FIG. 1. A nucleobase tip pinpoints its complementary nucleobase based on base-pair facilitated electron tunneling. (a) Formation of the complementary base-pairs between the nucleobase tip and the sample nucleobases leads to greatly facilitate electron tunneling in STM. Nucleobase tips can thus pinpoint the corresponding complementary nucleobases (b) The chemical structures for thiol derivatives of adenine (1), guanine (2), cytosine (3), and uracil (4) are shown, together with 2-mercaptobenzimidazole (MB) (5) and thiophenol (TB) (6).

FIG. 1(a) shows the principle of the present invention. The tunneling current measured by scanning tunneling microscopy (STM) between a nucleobase and its complementary nucleobase molecular tip was much facilitated compared to its non-complementary counterpart. Therefore, the single nucleobase can be analyzed by measuring the tunneling current between the target nucleobase and the molecular tip.

The molecular tip is a STM metal tip, and is chemically modified with adenine (A), guanine (G), cytosine (C) or thymine (T) (or uracil (U)). The STM metal tip is made from gold, platinum-Iridium alloy, and so on. For the chemical modification of the metal tip with the nucleobases, a derivative of nucleobase may be used. For example, thiol derivatives of nucleobases may be used for modifying gold tips.

The molecular tip is used for scanning a nucleic acid or a target nucleobase in a nucleic acid under STM system. The nucleic acid includes a single stranded genomic DNA or mRNA, cDNA synthesized from mRNA, or a chemically synthesized polynucleotides prepared by the known methods (for example, Carruthers, Cold Spring Harbor Symp. Quant. Biol. 47:411-418, 1982; Adams, J. Am. Chem. Soc. 105:661, 1983; Belousov, Nucleic Acid Res. 25:3440-3444, 1997; Frenkel, Free Radic. Biol. Med. 19:373-380, 1995; Blommers, Biochemistry 33:7886-7896, 1994; Narang, Meth. Enzymol. 68:90, 1979; Brown, Meth Enzymol. 68:109, 1979; Beaucage, Tetra. Lett. 22:1859, 1981; U.S. Pat. No. 4,458,066). In the case of detecting SNP in a nucleic acid, for example, a polynucleotide containing the potential SNP can be prepared by PCR method using a genomic DNA or total RNA from a subject and a primer set available from the know SNP databases (for example, http://SNP.ims.u-tolyo.ac.jp/index_ja.html). Since the SNP position in the polynucleotide can be known from the databases, it can be detected by the methods of the present invention, i.e., the pinpointing method or the typing method. According to the pinpointing method, in the case of the SNP being adenine (wild-type)—guanine (mutant) polymorphism, the tunneling current is measured by scanning cytosine tip on the target nucleobase. If the tunneling current increased, the target nucleobase should be guanine and SNP is judged as mutant-type. On the other hand, if the tunneling current increases with the uracil tip, the target nucleobase should be adenine and SNP is judged as wild-type. The pinpointing method of this invention also makes it possible to identify the position of a specific nucleobase in a nucleic acid, or determining a volume of specific base-pairs (ex. Extent of C-G rich).

SNP can be also detected by the typing method of this invention. That is, the types of the target nucleobase can be identified by scanning the four kinds of molecular tips.

In the sequencing method of this invention, nucleobases in a linear polynucleotide are sequentially scanned with the four kinds of molecular tips, and the tunneling currents between each nucleobase and each molecular tip are measured. The type of each nucleobase is sequentially determined as being complementary to the nucleobase type of the molecular tip by which the largest tunneling current is measured.

The nucleic acid should be arranged on a flat conductive substrate for precisely controlling the distance between the nucleobase and the molecular tip. For this purpose, the nucleic acid can be chemically or physically immobilized on a substrate such as Au (111) and so on.

Preferably, the bias voltage may be −400~−600 mV, and the tunneling current may be 1000~1400 pA.

EXAMPLES

The present inventions will be described in detail by the following Examples, but the present inventions are not limited to the Examples.

1. Materials and Methods

Preparation of Thiol Derivatives of Adenine, Guanine, Cytosine, and Uracil

As sample thiol derivatives of nucleobase (FIG. 1b), 4-amino-8-mercaptopyrmidine (1) (reference 19) and 2,4-hydroxy-6-mercaptopyridine (4) (reference 20) were synthesized, and the products were characterized by $^1$H NMR, $^{13}$C NMR, and elemental analysis. 4-Amino-2-hydoxy-6-mercaptopyrmidine (3: Sigma-Aldrich library of rare chemicals) and 2-amino-6-hydroxy-8-mercaptopurine (2: Acros) were recrystallized three times from ethanol prior to use. 2-Mercaptobenzimidazole (98%, Aldrich) and thiophenol (95%, Wako Pure Chemical, Osaka) were used without further purification. Instead of a thymine thiol derivative, a uracil derivative (4) was used because of its ease for synthesis.

1 (thiol derivative of adenine): $^1$H NMR (500 MHz, DMSO-$d_6$) δ 6.74 (s, 2H), 8.05 (s, 1H), 12.03 (s, 1H), 13.03 (s, 1H) $^{13}$C NMR (500 MHz, DMSO-$d_6$) δ 166.5; 152.6; 149.8; 147.3; 107.9; Anal. Calcd. for $C_5H_5N_5S$: C, 35.9; H, 3.0; N, 41.9 Found: C, 35.7; H, 3.2; N, 41.7

4 (thiol derivative of uracil): $^1$H NMR (500 MHz, DMSO-$d_6$) δ 5.61 (s, 1H), 8.60 (s, 1H), 10.98 (s, 1H), 12.05 (s, 1H). Anal. Calcd. for $C_4H_4N_2O_2S$: C, 33.3; H, 2.80; N, 19.43. Found: C, 33.1; H, 2.82; N, 19.45

Preparation of Gold (111) Substrate

An atomically flat gold (111) surface was epitaxially grown on a mica by vacuum deposition under a base pressure of about $2.0 \times 10^{-4}$ Pa ($1.5 \times 10^{-6}$ Toor) after the mica was preheated at 830 K. After the deposition, the substrate was annealed at 830 K for 10 h to obtain large terraces on the gold surfaces and cleaned before use by annealing with hydrogen-oxygen flame.

The Nucleobase Images Observed with Unmodified Gold Tips

Self-assembled monolayers (SAMs) for the thiol derivatives of adenine, guanine, cytosine and uracil on Au (111) in 1,2,4-trichlorobenzene solution were observed with unmodified gold STM tips. In the images, the sample nucleobases exhibited bright spots. The diameters of bright spots were 0.34±0.02 nm for adenine (FIG. 5), 0.35±0.04 nm for guanine, 0.33±0.02 nm for cytosine, and 0.33±0.06 nm for uracil, which are consistent with the size of the small axis of the pyrimidine or purine ring of the nucleobases. The values of height of probe tip were 47.7±6.2 pm for adenine, 46.9±5.2 pm for guanine, 47.9±6.5 pm for cytosine, and 45.8±5.2 pm for uracil, respectively. The results indicate that unmodified tips were unable to discriminate one nucleobase from the others in STM images.

Preparation of Self-assembled Monolayers (SAMs) of Neat/Mixed Nucleobases

For preparing the sample self-assembled monolayers (SAMs) of nucleobases (i.e., thiol derivatives of adenine, guanine, cytosine, and uracil), gold substrates were soaked into 10 mM sample ethanolic solutions (HPLC-grade ethanol, Wako Pure Chemical, Osaka, Japan) for 30 min, 45 min, or 1 h. After being taken out of the solution, the gold substrates were rinsed with ethanol to remove excess sample nucleobases physisorbed on the SAMs, and dried in vacuum. The sample adenine/guanine mixed SAMs were prepared from the aqueous 10 mM mixed solutions of adenine and guanine with their differing molar ratios.

Preparation of Nucleobase Modified Tip (Nucleobase Tip)

STM metal tips were prepared from a gold wire (0.25 mm diameter; Nilaco, Tokyo, Japan) by electrochemical etching in 3 M NaCl with ac 10 V and then washed in an ultrasonic bath or cleaned in piranha solution. For constructing nucleobase molecular tips, the gold tips were cleaned in piranha solution, and then immersed for 3 h in 10 mM ethanolic solution of thiol derivatives of nucleobases. The tips were then rinsed with ethanol and dried in a stream of argon or nitrogen.

STM Measurements of SAMs of Neat/Mixed Nucleobases

STM measurements were carried out on a Nanoscope E (Digital Instruments) at room temperature in a constant current mode. A drop (5 ul) of a 1,2,4-trichlorobenzene deposited on sample thio-base SAMs on Au (111) before the measurements. STM measurements were performed at the solution/gold interface under ambient condition at a bias voltage of −500 mV (sample negative), and a tunneling current of 1200 pA. It was confirmed that no polarity dependence was observed by applying the reversed potential. In the STM observation, about 45% of over 30 nucleobase tips exhibited the facilitated electron tunneling in each combination of nucleobases on tip and substrate, and the others exhibited the same STM images as those observed with unmodified gold tips The lack of the facilitation is most probably due to the absence of a nucleobase molecule at the very apex of the underlying gold tip at the atomic level.

Preparation and STM Measurements of Single Stranded Peptide Nucleic Acid (PNA) Oligomers Three kinds of single stranded eighteen-mer peptide nucleic acid (PNA) purified by HPLC, (i) $H_2N$-TTTTTTTTGTTTTTTTTT-$CONH_2$ (containing one guanine and seventeen thymines) (corresponds to SEQ ID NO: 2), (ii) $H_2N$-TTTTTTTGGTTTTTTTTT-$CONH_2$ (containing two guanines and sixteen thymines) (corresponds to SEQ ID NO: 1), and (iii) $H_2N$-TTTTTTTTTTTTTTTTTT-$CONH_2$ (containing eighteen thymines) (corresponds to SEQ ID NO: 3), were purchased (Fasmac. Co., Ltd., Kanagawa, Japan) and used for STM measurements without further purification. Sample substrates were prepared by depositing a drop (5 μl) of a 1,2,4-trichlorobenzene solution containing PNAs (concentration, 0.5-1.0 mM) onto a Au (111). STM measurements were performed at the solution/gold interface by immersion, under ambient condition at a bias voltage of −500 mV (sample negative) and a tunneling current of 1200 pA.

2. Results and Discussion

Figure 2:
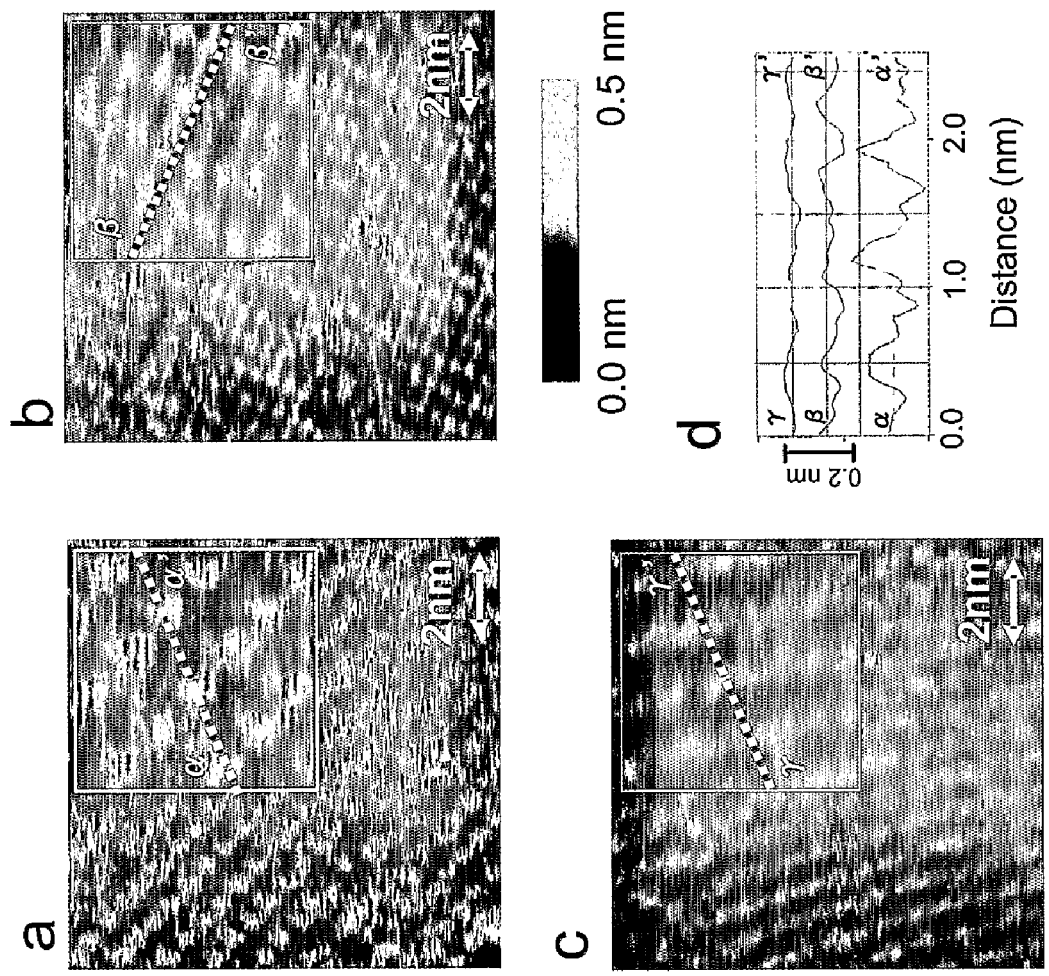
FIG. 2. Changes in the observed image contrast for guanines; comparison with unmodified, non-complementary, and complementary nucleobase tips. (a) An STM image of guanines observed with a complementary cytosine tip. (b) An STM image of guanines observed with a non-complementary adenine tip. (c) An STM image of guanines observed with an unmodified tip. The magnified images ($2.5 \times 2.5$ nm$^2$) of image a, b, and c are shown in the insets, respectively. (d) Cross-sectional profiles along the dashed lines ($\alpha$-$\alpha'$, $\beta$-$\beta'$, and $\gamma$-$\gamma'$) in the inset image a, b, and c, respectively. The y-axis of the cross-sectional profiles represents the extent of electron tunneling, as measured by the height of the tip from a given position to meet the constant current mode in the STM measurement. (e) Extents of electron tunneling between tip and sample nucleobases. The mean values (n=10) of the extents of the observed electron tunneling between nucleobase tips (i.e., adenine, guanine, cytosine, and uracil tips) and sample nucleobases (i.e., adenine, guanine, cytosine, and uracil) represented in "height (pm)" of the tips (see image d caption). Those with irrelevant tips (i.e., unmodified, MP, and TP tips) were also obtained, for comparison, under otherwise identical conditions. (f, g) Extents of electron tunneling for adenine (red column) and guanine (blue column) images in pure monolayers and in mixed monolayers. The results of f and g were obtained with cytosine and uracil tips, respectively.
Figure 2:
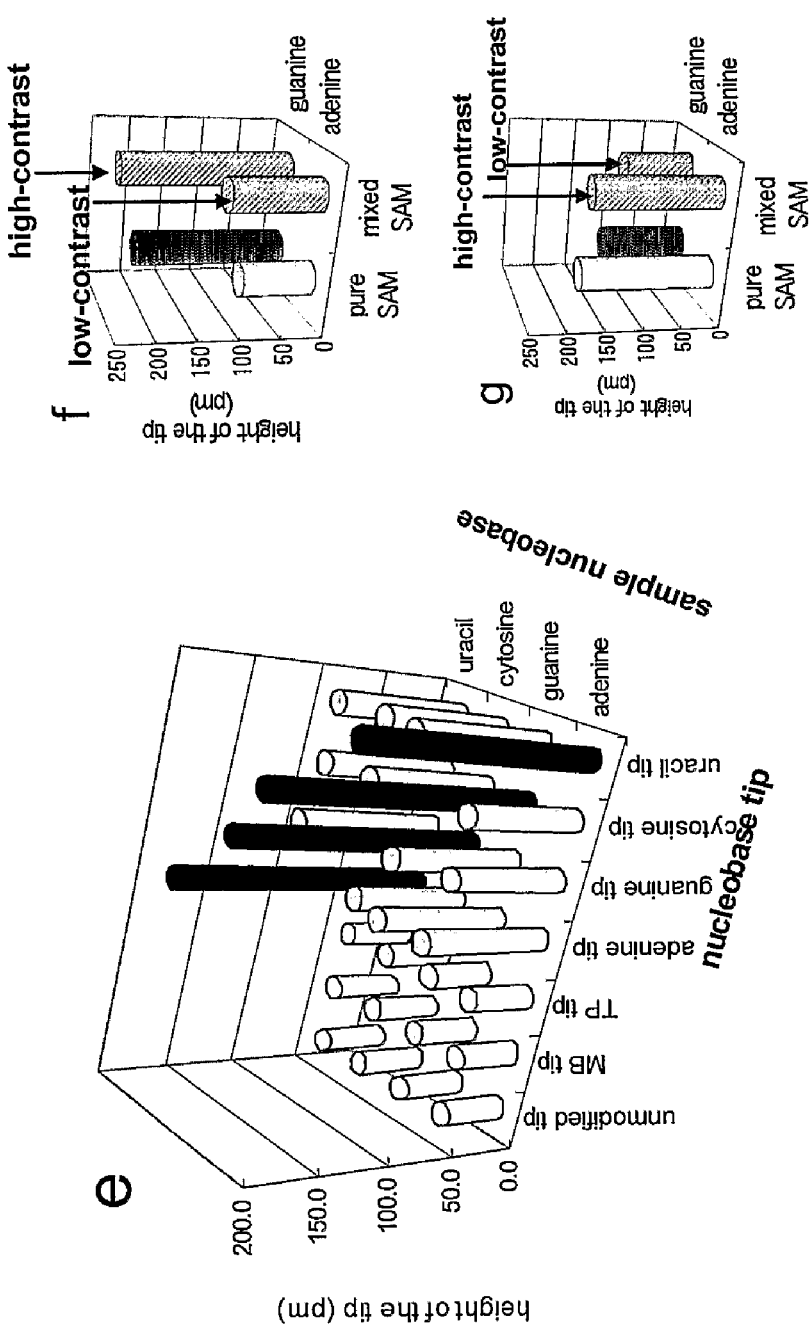
Figure 5:
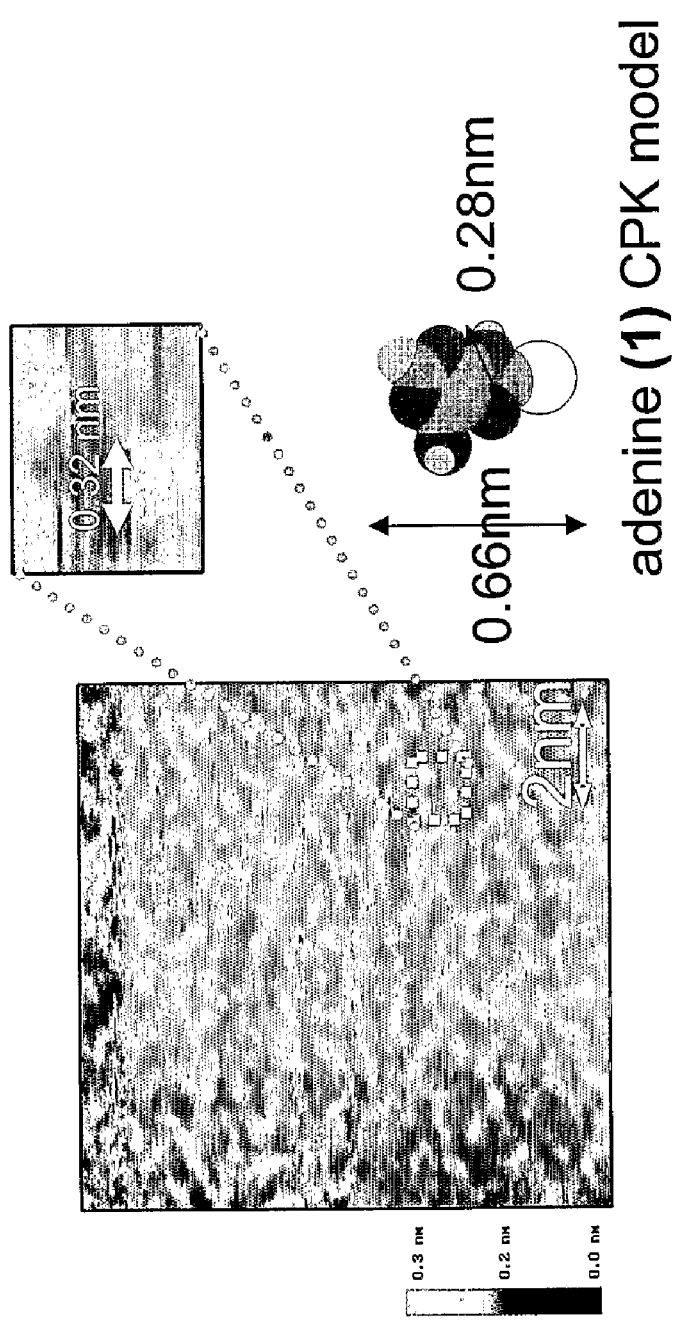
FIG. 5. An STM image of an adenine SAM observed with an unmodified gold tip and the Corey-Pauling-Koltun (CPK) model of the thiol derivative of adenine (1). The scan area was 10×10 nm² and the bias voltage was −500 mV (sample negative), and the tunneling current was 1,200 pA (constant current mode) The diameters of the adenine images were 0.34±0.02 nm, which is comparable to the size of the small axis of the pyrimidine from an adenine CPK model. This result indicates that the sample adenines stand vertically on a gold substrate.

The nucleobase molecular tips were prepared by chemical modification of underlying metal tips with thiol derivatives of adenine, guanine, cytosine, and uracil (see Methods) (chemical structures; FIG. 1b, and their preparations), and the outmost single nucleobase adsorbate probes intermolecular electron tunneling to or from a sample nucleobase molecule. Importantly, the tunneling current increases when sample and tip molecules form a chemical interaction that provides overlap of electronic wave functions between them. The current increase is ascribed to the facilitated electron tunneling through the overlapped electronic wave functions. Electron tunneling observed here occurs without any net chemical oxidation/reduction of the involved bases. FIGS. 2a, 2b, and 2c show typical STM images of guanine SAMs observed with complementary cytosine tips, non-complementary adenine, and unmodified tips, respectively (see Methods). Their respective cross-sectional profiles of the images are also shown in FIG. 2d, which represents the extent of electron tunneling between the tip and nucleobase. The complementary cytosine tip exhibited the most facilitated electron tunneling and therefore the brightest guanine images among the three tips. Similarly, for adenine, cytosine and uracil, their complementary nucleobase tips gave the brightest images of their counterparts, the results of which are shown in FIG. 2e together with those using irrelevant tips for validation The inventors have differentiated the complementary nucleobases from the non-complementary ones by the tip heights for the sample nucleobases in absolute terms. The height is a quantitative measure of the current, because the tunneling current I is related to the tip height h by the relation as $I \propto \exp(-2kh)$, where $k = h^{-1}(2m\phi)^{1/2}$ and $\phi$ is the work function of the sample (reference 9). The tip height h is usually recorded rather than the current I for the instrumental convenience, keeping the current I constant. For example, with the cytosine tips, the heights of the tip were found to be 197±23 pm for the complementary guanines (FIG. 2e: black column), and 102±5 pm, 98±9 pm, and 99±7 pm for the non-complementary adenines, uracils, and cytosines, respectively (FIG. 2e: yellow column). These heights quantitatively represent the tunneling currents flowing within the base-pairs. On the contrary, with unmodified tips, or with gold tips modified with 2-mercaptobenzimidazole (MB) and thiophenol (TP) (chemical structures, FIG. 1b), which have a pyrimidine- and pyridine-like structure, respectively, but no particular functional groups for hydrogen-bond formation with nucleobases, selective facilitation of electron tunneling was not detected for any nucleobases (FIG. 2e: yellow column), as shown in an STM image (FIG. 5). Taken all together, it is concluded that the complementary combinations of the tip and sample base-pairs facilitated the largest electron tunneling compared to the non-complementary combinations, and particular nucleobases were thus discriminated from other nucleobases in STM images by using the complementary nucleobase tips.

Figure 3:
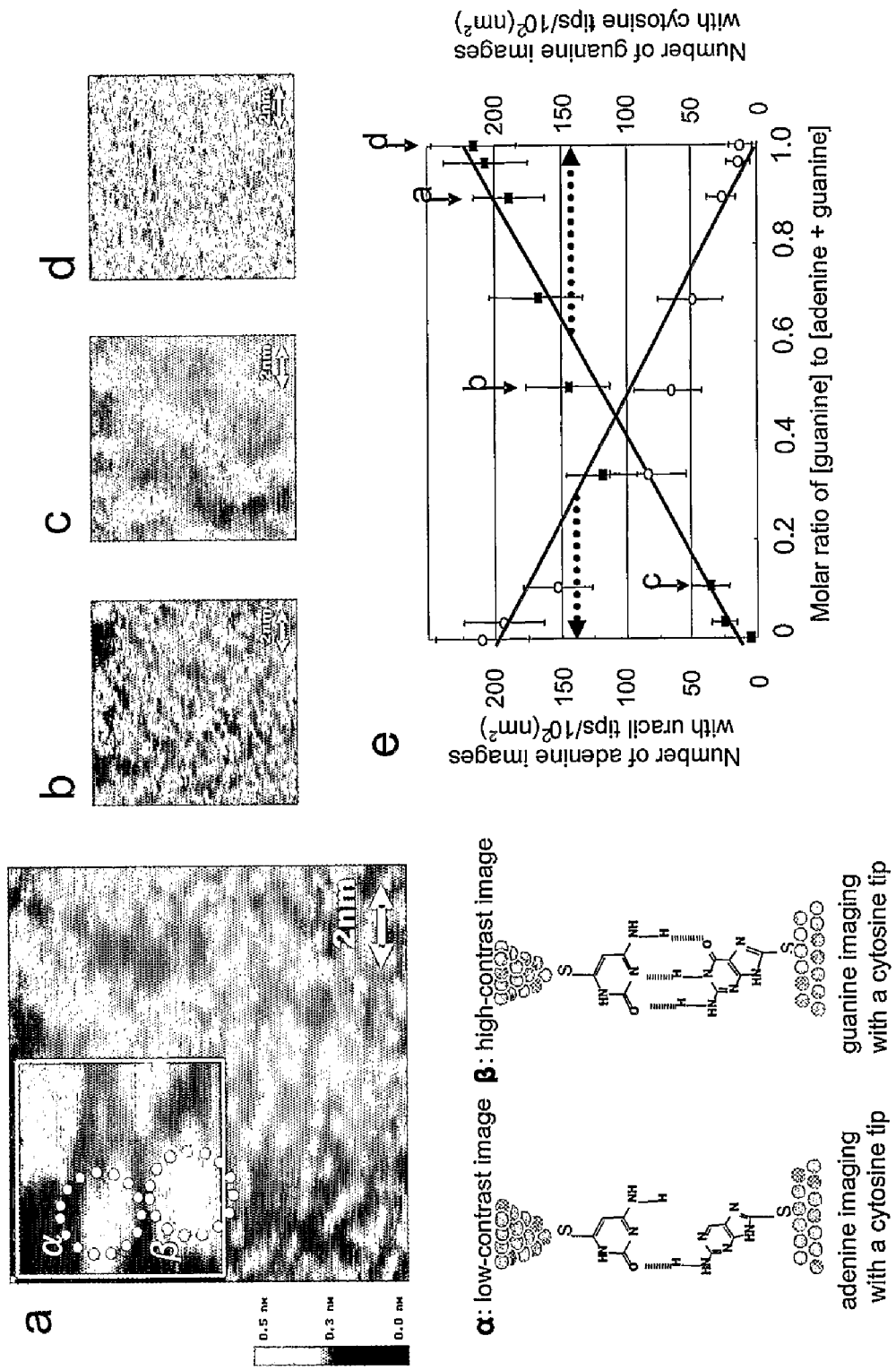
FIG. 3. Selective illumination of complementary nucleobases in guanine/adenine mixed SAMs. (a, b, c) STM images ($10 \times 10$ nm$^2$) of adenine/guanine mixed SAMs prepared from the sample solutions, of which molar ratio of guanine to adenine are 10.0:1.0 for a, 1.0:1.0 for b, and 1.0:10.0 for c, respectively. The magnified area of image a ($1.5 \times 1.5$ nm$^2$) is shown in the inset, where low-($\alpha$) and high-($\beta$) contrast images exhibit guanine and adenine, respectively. (d) An STM image ($10 \times 10$ nm$^2$) of a neat guanine SAM. The image a, b, c, and d were obtained with cytosine tips. (e) The number of guanine images (■) increased and that of adenine images (○) decreased, respectively, in proportion to the molar ratio of [guanine] to [guanine+adenine] in the sample nucleobase mixed solutions. The number of adenines and guanines were counted respectively in an image ($10 \times 10$ nm$^2$) of an adenine/guanine mixed SAM, and the procedure was repeated for another nine images. The results were averaged therefrom (n=10).
Figure 6:
FIG. 6. An STM image of an adenine/guanine mixed SAM observed with an unmodified gold tip. The scan area was 7.0×7.0 nm² and the bias voltage was −500 mV (sample negative), and the tunneling current was 1,200 pA (constant current mode).

In the mixed nucleobase SAMs (see Materials and Methods), nucleobase tips were capable of pinpointing respective complementary nucleobase images in the presence of other nucleobases. FIG. 3a shows a typical STM image of an adenine/guanine mixed SAM observed with a cytosine tip. As shown in the inset of FIG. 3a and FIG. 2f, the cytosine tip gave a high- and low-contrast image for the complementary guanine and non-complementary adenine, respectively. The number of the high-contrast guanine images increased in proportion to the molar ratio of [guanine] to [guanine+adenine] in the sample mixed solution for the SAM (compare FIGS. 3b, 3c, and 3d), the results of which are shown in FIG. 3e. Similarly, uracil tips were capable of selectively pinpointing the complementary adenine images in the presence of non-complementary guanines in the SAM (FIG. 2g), and the number of the high-contrast adenine images also increased in proportion to molar ratio of [adenine] to [guanine+adenine]

in the sample solutions as shown in FIG. 3e. These results indicate that in the mixed nucleobase SAMs, the large electron tunneling through the complementary base-pairing allows us to pinpoint a particular nucleobase in the presence of other nucleobases. On the other hand, with unmodified tips, the four bases were observed as identical images even in the mixed SAM (FIG. 6). This indicates that the chemical differentiation of complementary bases with the nucleobase tips was not due to the difference in heights of the four bases. Also, MB and TP tips did not show selective large facilitation of electron tunneling (FIG. 2e: yellow column), confirming that the observed difference is solely due to the hydrogen-bonds of complementary base-pairs between bases on a tip and substrate.

The inventors have earlier reported on the use of hydrogen-bond based molecular tips for selective STM imaging of hydrogen-bond acceptor or donor molecules and functional groups, as well as on the use of other chemical interaction based molecular tips; metal-coordination-bond based molecular tips for selective STM imaging of metal species in metalloporphyrins (reference 5), and charge-transfer interactions based molecular tips for that of electron-rich porphyrin rings (reference 8). Upon tailor-making the molecular tips with differing extents of hydrogen bond acidity or basicity, the inventors have succeeded in selectively pinpointing particular functional groups in sample molecules, including hydroxy, carboxy, carboxylate, ether oxygens and its orientations, and a free-base porphyrin center (references 1-8). The inventors herein added another example of hydrogen-bond-facilitated electron tunneling, i.e., complementary base-pair facilitated electron tunneling (FIG. 1a). For example, before the cytosine tip was placed on a guanine base, the guanine base does not possess any greater electron density compared to other bases, but instead a greater electron density is induced along the hydrogen bonding plane upon placing the cytosine tip on the guanine base. This induced increase in electron density translates into a greater electronic coupling between the two bases and thus an increase in the tunneling current between them. As a result, nucleobase tips gave large extents of electron tunneling currents only for its complementary bases. The direction of electron flow between bases on a tip and a substrate did not affect the extent of electron tunneling through the same combination of the material (FIG. 2e): for instance, cytosine and guanine tips gave the same extent of electron tunneling to their counterpart complementary bases. Therefore, the extent of overlap of electron wave functions of the base-pairs solely plays the requisite role.

The formations of the specific hydrogen bonds through complementary base-pairs require that coplanar configurations of the bases be achieved on the tip and surface. Although the plane of bases may likely be oriented randomly in mixed monolayers (FIG. 6) and orderly in pure monolayers (FIG. 2c), the nucleobase tips gave the selective large facilitation of electron tunneling for its complementary bases both in the pure and mixed monolayers, (FIG. 2a and FIG. 3a-d), indicating that the base-base coplanar orientation was in fact achieved, and thus the specific hydrogen-bonds between the complementary base-pairs were formed. The base-base coplanarity is attained probably by the rotation of a carbon-sulfur bond in the thio-base on a tip, which is well-known even in the close-packed structure of thiolate SAMs (reference 10). Therefore, the complementary bases in the SAM were exclusively differentiated. Although other hydrogen-bonds, such as the Hoogsteen and G:U Wobble base-pairs, could be formed between bases on the tip and sample substrate, they were found to give only a small tunneling current similar to those of non-complementary base-pairs (FIG. 2e-g), and did not thereby interfere with the chemical differentiation based on complementary base-pairs. There exists a branch of supramolecular chemistry to use the paradigm of individual nucleobases. The thermodynamic stabilities and related characteristics of these nucleobases have been extensively studied, and many researchers have reported Watson-Crick type specific interactions between monomeric nucleobases (reference 11) These reports substantiate the profound specificity observed in the present study, including strong preference for Watson-Crick binding and rejection of Hoogsteen and Wobble base-pairing.

Hole and electron transfer in a DNA strand occur via two pathways, along the DNA strand (intrastrand pathway), and through the base-pairs (interstrand pathway). In the interstrand pathway, electron transfer occurs preferentially through the hydrogen-bonds of complementary base-pairs (reference 21). Barton and her colleagues constructed the DNA double strands that were linked to a donor and acceptor located on the different strand, respectively, and found that larger electron transfer occurred through the interstrand connection of the complementary double strands relative to the other double strands containing mispairs. On the other hand, in the intrastrand pathway, the electron hopping is known to occur through a pi-pi stacking interaction of base-pairs (references 21-26). Of the two pathways, only the interstrand pathway is to be compared with the present results.

The molecular tips directly detected intermolecular electron tunneling between sample and tip molecules, and revealed the tunneling facilitation through chemical interactions that provide overlap of respective electronic wave functions, that is, hydrogen-bond (references 1-8), metal-coordination bond (reference 15), and charge-transfer interactions (reference 8). The inventors have extensively studied chemical selectivity toward various functional groups based on hydrogen bond interactions. The chemical selectivity can be tailored by controlling the extent of the hydrogen bond acidity or basicity of the molecular tips (reference 7). Larger facilitation of electron tunneling was observed at ether oxygens in a favorable orientation than those in unfavorable orientations, allowing us to discriminate between these differently oriented functional groups. These results substantiate the facilitated electron tunneling through hydrogen bond interactions, which resulted in pinpointing complementary nucleobases in the present study. Hydrogen-bond-mediated electron-transfer process has been of great interests and studied by several groups using photo-induced electron-transfer with acceptor/donor markers (reference 27) because of its fundamental importance in chemical reaction processes, and crucial roles in biological electron-transfer processes.

Figure 4:
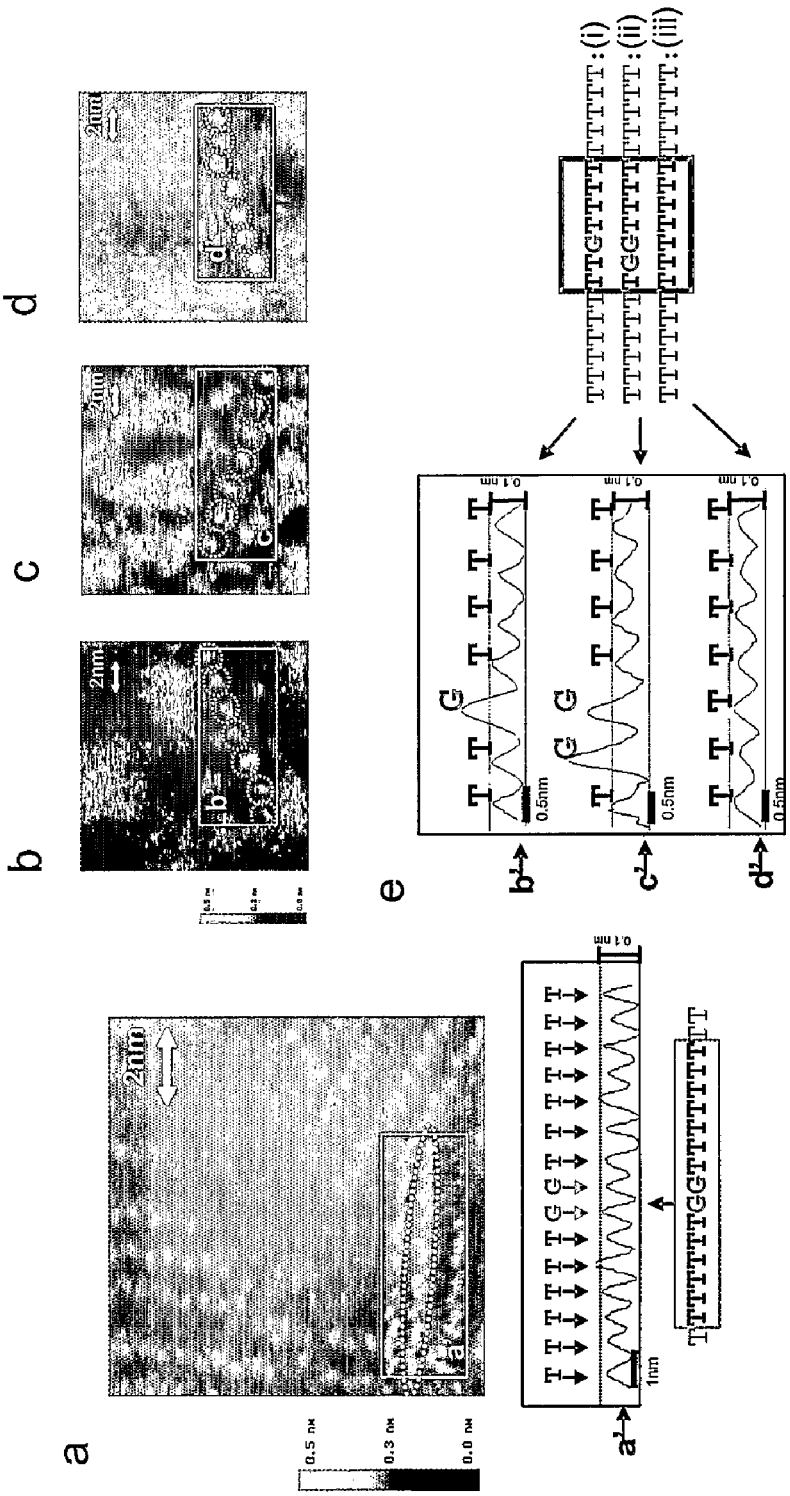
FIG. 4. SNP typing in 18-mer single stranded peptide nucleic acids. (a) An STM image ($10 \times 10$ nm$^2$) with an unmodified tip of single stranded eighteen-mer PNAs, the sequence of which is TTTTTTTGGTTTTTTTTT (SEQ ID NO: 1). A cross-sectional profile along the strand circled by white dots in the inset a' ($3.5 \times 10$ nm$^2$) is also shown. White arrow drawn in the image pinpointed one end of a PNA strand. (b, c, d) STM images ($15 \times 15$ nm$^2$) with cytosine tips of three kinds of PNA strands; TTTTTTTTGTTTTTTTTT (SEQ ID NO: 2), TTTTTTTGGTTTTTTTTT (SEQ ID NO: 1), and TTTTTTTTTTTTTTTTTT (SEQ ID NO: 3), are shown in b, c and d, respectively. The magnified images ($2.0 \times 5.0$ nm$^2$) of image b, c, and d are shown in the inset b', c', and d', respectively. (e) Cross-sectional profiles of a row of base images along the PNA strand circled by white dots in the inset b', c', and d', respectively. The y-axis of the cross-sectional profiles represents the extent of electron tunneling along the strands.

An example of the detection of particular nucleobases was demonstrated here with the present method in an 18-mer strand of a peptide nucleic acid (PNA), an analogue of DNA) (reference 12). A typical STM image with an unmodified tip of a PNA strand is shown in FIG. 4a, indicating that bases in the strand were observed as rows of bright spots and the components of the strand, guanines and thymines, were not discriminated. On the contrary, cytosine tips pinpointed the complementary guanines among the non-complementary thymines in the strands (FIG. 4b-d and the insets). The extent of electron tunneling along the strands shows that a single and double base substitution in the strands were distinguished with the cytosine tip (FIG. 4e).

In conclusion, the inventors found that hydrogen-bond-mediated electron tunneling occurs with the complementarity between the tip nucleobase and sample nucleobase. Increase in the electron tunneling is capable of electrically pinpointing each nucleobase. Until now, STM observations of nucleobases (references 13-15) and DNA oligomers (references 16-18) have been reported, but these studies failed to identify the chemical species of nucleobases because of their poor chemical selectivity of the STM images. The present approach made it possible to pinpoint particular nucleobases. Enhancement of electron tunneling occurred at specific functional groups and chemical species on the basis of hydrogen bond, metal-coordination bond, and charge-transfer interactions, respectively, and as a result, allowed to identify the location of the specific chemical species and functional groups. This technique may be coined "intermolecular tunneling microscopy" as its principle goes, and is of general significance for novel molecular imaging of chemical identities at the membrane and solid surfaces.

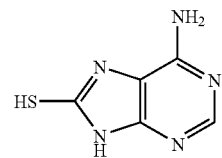
(I)

The invention claimed is:

1. A method for pinpointing a target nucleobase in a nucleic acid, which comprises:

scanning a nucleobase molecular tip on the nucleic acid to form multiple hydrogen bonds between the nucleobase molecular tip and the target nucleobase, wherein the nucleobase molecular tip is a gold tip chemically modified with a nucleobase complementary to the target nucleobase and thereby capable of forming multiple hydrogen bonds with the target nucleobase, and the complementary nucleobase is selected from the following thiol derivatives of adenine (I), guanine (II), cytosine (III) and uracil (IV);

-continued

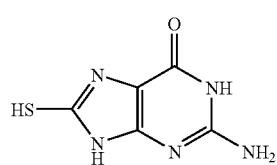
(II)

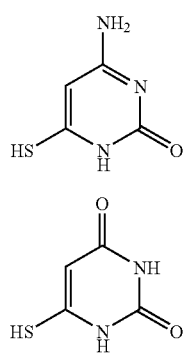

measuring the tunneling current due to hydrogen bonds between each nucleobase and the nucleobase molecular tip with scanning tunneling microscopy; and pinpointing the target nucleobase as the nucleobase from which the tunneling current is facilitated upon scanning the nucleobase molecular tip.

2. A method for typing a target nucleobase in a nucleic acid to form multiple hydrogen bonds between the nucleobase molecular tip and the target nucleobase, which comprises:

scanning four nucleobase molecular tips on the nucleic acid, wherein the four nucleobase molecular tips are gold tips chemically modified with the following thiol derivatives of adenine (I), guanine (II), cytosine (III) and uracil (IV), respectively;

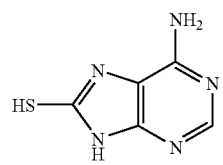

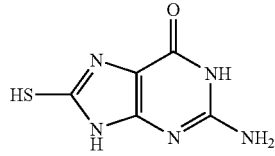

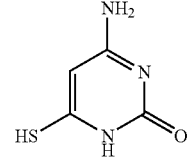

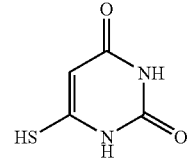

measuring the tunneling currents due to hydrogen bonds between the target nucleobase and each nucleobase molecular tip with scanning tunneling microscopy; and determining the type of the target nucleobase that is complementary to the nucleobase on the nucleobase molecular tip by which the largest tunneling current is measured.

3. A method for sequencing a nucleic acid, which comprises:

scanning sequentially four nucleobase molecular tips on the nucleic acid to form multiple hydrogen bonds between each nucleobase molecular tip and the complementary nucleobase, wherein the four nucleobase molecular tips are gold tips chemically modified with the following thiol derivatives of adenine (I), guanine (II), cytosine (III) and uracil (IV), respectively;

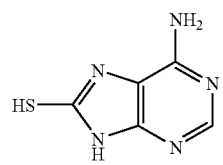

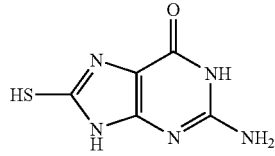

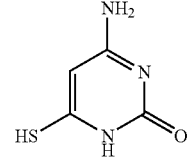

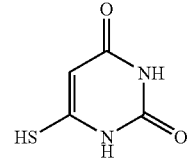

measuring the tunneling currents due to hydrogen bonds between each nucleobase and each nucleobase molecular tip with scanning tunneling microscopy; and determining the type of each nucleobase that is complementary to the nucleobase on the nucleobase molecular tip by which the largest tunneling current is measured thereby sequencing the nucleic acid.

4. A nucleobase molecular tip for scanning tunneling microscopy, which is a gold tip chemically modified with the following thiol derivative of adenine (I), guanine (II), cytosine (III) or uracil (IV):

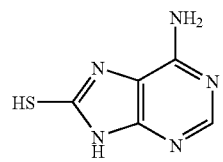

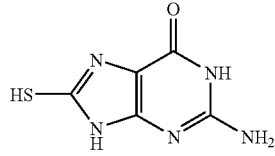

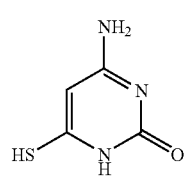
(III)
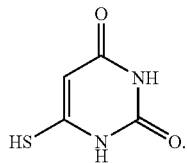
(IV)
5. A set of four nucleobase molecular tips for scanning tunneling microscopy, which consists of four gold tips chemically modified with the following thiol derivatives of adenine (I), guanine (II), cytosine (III) and uracil (IV), respectively:
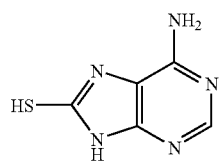
(I)
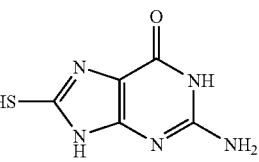
(II)
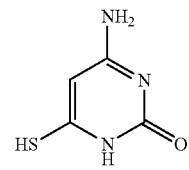
(III)
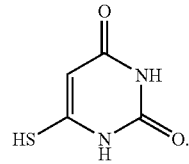
(IV)
* * * * *

SEQUENCE LISTING

<160> NUMBER OF SEQ ID NOS: 3

<210> SEQ ID NO 1
<211> LENGTH: 18
<212> TYPE: DNA
<213> ORGANISM: Artificial sequence
<220> FEATURE:
<223> OTHER INFORMATION: Description of artificial sequence: synthetic oligonucleotide

<400> SEQUENCE: 1
tttttttggt tttttttt                                                 18

<210> SEQ ID NO 2
<211> LENGTH: 18
<212> TYPE: DNA
<213> ORGANISM: Artificial sequence
<220> FEATURE:
<223> OTHER INFORMATION: Description of artificial sequence: synthetic oligonucleotide

<400> SEQUENCE: 2 tttttttttgt tttttttt                                                18

<210> SEQ ID NO 3
<211> LENGTH: 18
<212> TYPE: DNA
<213> ORGANISM: Artificial sequence
<220> FEATURE:
<223> OTHER INFORMATION: Description of artificial sequence: synthetic oligonucleotide

<400> SEQUENCE: 3 ttttttttttt tttttttt                                                18